United States Patent [19]

Fields

[11] 4,095,029

[45] June 13, 1978

[54] 2-HYDROXY-3-ALKYLSULFOXYPROPYL-1 ESTERS OF ARENE POLYCARBOXYLIC ACIDS

[75] Inventor: Ellis K. Fields, River Forest, Ill.

[73] Assignee: Standard Oil Company (Indiana), Chicago, Ill.

[21] Appl. No.: 760,013

[22] Filed: Jan. 17, 1977

[51] Int. Cl.² ............... C07C 69/82; C07C 147/14

[52] U.S. Cl. ............... 560/87; 260/287 AR; 260/287 D; 260/287 CE; 260/294.8 B; 260/294.8 C; 260/294.8 F; 260/347.2; 260/332.2 R; 560/20; 560/21; 560/23; 560/56; 560/59; 560/64; 560/65; 560/73; 560/74; 560/80; 560/83; 560/84; 560/85; 252/354; 252/395; 252/406; 252/549; 424/308

[58] Field of Search ............... 260/475 P; 560/80, 87, 560/83, 84, 85, 20, 21, 23, 56, 59, 65, 73, 74, 64

[56] References Cited

U.S. PATENT DOCUMENTS 2,645,659   7/1953   Morris et al. ............... 560/87

*Primary Examiner*—Jane S. Myers
*Attorney, Agent, or Firm*—William C. Clarke; Arthur G. Gilkes; William T. McClain

[57] ABSTRACT

2-Hydroxy-3-alkylsulfoxypropyl-1 esters of arene polycarboxylic acids.

9 Claims, No Drawings

2-HYDROXY-3-ALKYLSULFOXYPROPYL-1 ESTERS OF ARENE POLYCARBOXYLIC ACIDS

BACKGROUND OF THE INVENTION

This invention relates to 2-hydroxy-3-alkylsulfoxypropyl-1 esters of arene polycarboxylic acids. More particularly, this invention relates to 2-hydroxy-3-alkylsulfoxypropyl-1 esters of phenylpolycarboxylic acids, 2-hydroxy-3-alkylsulfoxypropyl-1 esters of biphenylpolycarboxylic acids, 2-hydroxy-3-alkylsulfoxypropyl-1 esters of naphthylpolycarboxylic acid esters, 2-hydroxy-3-alkylsulfoxypropyl-1 esters of anthranylpolycarboxylic acids, and 2-hydroxy-3-alkysulfoxypropyl-1 esters of phenanthrylpolycarboxylic acids.

For convenience these compounds are referred to as 2-hydroxy-3-alkylsulfoxypropyl-1 esters of arenepolycarboxylic acids. These compounds possess biocidal properties, have high toxicity to fungicidal growths, have rust inhibiting properties and demonstrate surfactant properties, and can be used as wear preventing additives in lubricating greases.

Organic sulfur compounds are of considerable industrial importance. Novel organic sulfur compounds with characteristics suitable for use in soluble oil compositions, tertiary oil recovery micellar fluids, and miscellaneous uses such as pesticides are of extensive utility. For example, steam turbine and other industrial oils can be stabilized against the rusting of ferrous parts should water become mixed with the oil. An important use of soluble oils is as a lubricating and cooling agent in the cold working of metals such as in grinding, cutting and threading operations. For this use, the soluble oil is dispersed in from about 10 to 80 or more times its own volume of water and circulated over the contact point of the working tool and the metal being worked on. Frequently, difficulty is encountered in this type of operation due to the tendency of the soluble oil emulsion or dispersion to cause rusting of metals in contact with such emulsions, particularly ferrous metals, and also because in the course of time, these emulsions or dispersions develop strong, putrid, undesirable odors if the soluble oil composition does not contain a bactericide.

DESCRIPTION OF THE PRIOR ART

This invention relates to esters of beta hydroxy sulfoxides and more particularly to arene esters of $\beta$-hydroxy sulfoxides, their preparation from allyl esters of arenepolycarboxylic acids and their use as surface active agents, rust inhibitors, and biocides.

The preparation of sulfoxides in the prior art has been through the oxidation of sulfides using (a) peroxides, peracids and ozone, (b) chromic acid, (c) nitric acid and oxides of nitrogen, (d) iodosobenzene and derivatives, and (e) some miscellaneous methods such as using manganese dioxide, lead tetraacetate, potassium permanganate, etc.

In the prior art, $\beta$-hydroxysulfoxides are well known. Kharasch and co-workers reported in 1950, *J. Org. Chem.*, 16, 524 (1951) that thiols and alpha olefins were co-oxidized by molecular oxygen at room temperature. The air oxidation of a mixture of an "active" olefin, such as styrene and a mercaptan, was found to give among other products, $\beta$-hydroxy sulfoxides. This reaction was used to prepare 2-hydroxy-2-phenethyl-2-phenethyl sulfoxide from styrene and phenethyl mercaptan. The precursor of the $\beta$-hydroxysulfoxide, the $\beta$-hydroperoxide sulfide, has been isolated (A. A. Oswald, *J. Org. Chem.*, 24, 443 (1959)). Preparation of the isomers of trans-2-phenylthionyl-1-indanol has been reported (J. Ford et al, *Tetrahedron*, 4, 325 (1958) as well as methyl-$\beta$-hydroxyalkyl sulfoxide, U.S. Pat. No. 3,247,258. However, $\beta$-sulfoxides of allyl esters of arene polycarboxylic acids have not been previously known. In specific embodiments of this invention, detergent compositions containing these novel compositions are contemplated, as well as lubricant compositions requiring rust inhibition and biocidal activity as in soluble oils and as an antiwear additive for lubricating grease.

SUMMARY OF THE INVENTION

Novel polysulfoxide compounds are prepared by co-oxidation of allyl esters of arenepolycarboxylic acids and thiols in the presence of molecular oxygen and a dye sensitizer. The $\beta$-hydroxysulfoxides are 2-hydroxy-3-alkyl-sulfoxypropyl-1 esters of arenepolycarboxylic acids. The arene moiety can be derived from benzene, biphenyl, naphthalene, anthracene and phenanthrene compounds. The alkyl moiety can be selected from the group consisting of alkyl moieties containing 1 to 26 carbon atoms, and aralkyl moieties, alkylated aryl moieties, heterocyclic alkyl moieties, and cycloalkyl moieties containing 6 to 22 carbon atoms. The arene and alkyl moieties can be substituted with halo-, nitro- and alkoxy groups.

DETAILED DESCRIPTION OF INVENTION

Novel polysulfoxide compounds of 2-hydroxy-3-alkylsulfoxypropyl-1 esters of arene polycarboxylic acids are derived from an olefin and a thiol and can be characterized as being a class of oxidized thioether derivatives of alkyl esters of arenepolycarboxylic acids. The particular polysulfoxide is dependent upon the allyl arene polycarboxylic acid used and the thiol of mercaptan used.

The object of this invention accordingly is to provide a new class of polysulfoxide compounds. Another object is to provide new pesticidal compounds which possess a molecular configuration that allows the preparation of water-soluble derivatives for use in soluble oils. Another object is to provide a sulfur-containing compound suitable for use in lubricants as a wear-preventing additive. Another object is to provide a family of sulfur-containing compounds with surfactant properties suitable for use in lubricating oils of many types. Other objects appear hereinafter.

For purposes of this invention, the term "arene" is defined, as in Hackh's Chemical Dictionary, 4th Ed., McGraw-Hill (1969) as indicating a hydrocarbon containing at least one aromatic ring, typified by benzene, naphthalene, anthracene, and phenanthrene. The term "radical" is defined, as in Hackh's Chemical Dictionary, 4th Ed., as a group of atoms that behaves as a single atom in a chemical reaction.

For purposes of this invention, the term "alkyl moiety" is defined as including monovalent chain saturated hydrocarbon groups containing 1 to 22 carbon atoms, i.e., methyl, ethyl, propyl, isopropyl, butyl and isobutyl, 2-ethylhexyl, amyl, hexyl, heptyl, dodecyl, octyl, isotridecyl, stearyl, oleyl, and tetracosyl groups. The term "aralkyl moiety" is defined as including groups composed of monovalent chain saturated hydrocarbon moieties containing from 1 to 22 carbon atoms attached to aromatic moieties containing 6 to 18 carbon atoms such as phenyl, biphenyl, naphthyl, anthranyl, etc. The term "alkylated aryl moieties" is defined as including aromatic moieties containing 6 to 18 carbon atoms, i.e., phenyl, biphenyl, naphthyl, anthranyl, etc., the said aromatic moieties being substituted with alkyl groups up to ten in number, the said alkyl groups containing from one to four carbon atoms. The term "heterocyclic alkyl moieties" is defined as a group containing an unsaturated cyclic or ring structure of five or more atoms in the ring in which one or more of the atoms in the ring is an element other than carbon and can be oxygen, nitrogen and/or sulfur, the ring structure attached to an alkyl group containing 1 to 22 carbon atoms, the said ring structure containing up to three cyclic analogues. Examples are thienyl, pyridyl, benzothienyl, thienobenzenyl, quinolyl, isoquinolyl, dibenzothienyl and phenanthridyl groups. The term "cycloalkyl moieties" is defined as including saturated cyclic moieties such as the monocyclic groups cyclohexyl, cycloheptyl, cyclooctyl, the dicyclic groups and the tricyclic groups such as decahydronaphthalene (decalin), perhydroanthracene and perhydrophenanthrene containing up to 40 carbon atoms. The above same groups can be substituted or unsubstituted, containing such substituents such as halogen (fluorine, chlorine, bromine and iodine), nitro and alkyl groups, alkoxy groups such as methoxy, ethoxy, propoxy, butoxy, decyloxy and dodecyloxy groups. Examples of these several groups and moieties are given in the discussion of the starting compounds.

The polysulfoxides of this invention are poly(2-hydroxy-3-alkylsulfoxypropyl-1)$_n$ esters of arenepolycarboxylic acids wherein $n$ is 2 to 6 and have the following formula:

where R is an arene polyvalent radical derived from the group of compounds consisting of benzene, biphenyl, naphthalene, anthracene and phenanthrene compounds having a total of 6 to 14 ring carbon atoms. Accordingly, R is a carbocyclic aromatic radical individually selected from the carbocyclic aromatic radicals of these compounds. R' is a monovalent radical bound to a sulfoxy group. R' is derived from the thiol R'SH and is selected from the group of moieties consisting of alkyl moieties containing from 1 to 22 carbon atoms, and aralkyl moieties, alkylated aryl moieties, heterocyclic alkyl moieties and cycloalkyl moieties containing 4 to 40 carbon atoms, the ring radicals of said moieties being selected from the group consisting of phenyl, biphenyl, cyclohexyl, pyridyl, quinolyl, isoquinolyl radicals. The said moieties of R and R' can be substituted and unsubstituted, said substitutions being individually selected from the group consisting of halogen, nitro and alkoxy moieties. The integer $n$ is 2 to 6. X is hydrogen or halogen (fluorine, chlorine, bromine, iodine), nitro and R"O where R" is an alkyl group of 1 to 12 carbon atoms (methyl, ethyl, propyl, butyl, octyl, decyl, dodecyl, etc.) and $m$ is 1 to 6.

R' of the thiol R'SH can be a straight or branched chain alkyl group containing 1 to 22 carbon atoms, preferably 4 to 18 carbon atoms; an aralkyl group, an alkylated aryl group, a heterocyclic alkyl group, a cycloalkyl group, the last four containing 4 to 40 carbon atoms, preferably 6 to 24 carbon atoms, and the same groups containing substituents such as halogen, nitro or alkoxy groups. Examples are thiol derivatives of n-butyl chloride, n-hexyl iodide, isobutyl bromide, n-dodecyl bromide, isostearyl iodide, benzyl chloride, p-methylbenzyl bromide, β-phenethyl bromide, α-chloromethyl naphthalene, 4-chloro-1-iodobutane, β-nitrobutyl bromide, 3-methoxybutyl chloride, 1-diethylamino-ethyl chloride, 4-nitrobenzyl chloride, 4-chlorobenzyl chloride, 4-chloromethyl anisole, 4-diethylaminobenzyl chloride, 2-chloromethyl furan, 3-chloromethyl thiophene, 4-chloromethylpicoline, cyclohexyl bromide, 1-fluoro-4-bromocyclohexane, 2-methoxy cyclopentyl chloride, 6-nitro-2-chloromethyl quinoline, and 6-diethylamino-2-chloro-methyl isoquinoline.

Typical compounds of this invention include
bis-(3-dodecylsulfoxy-2-hydroxypropyl) terephthalate
bis-(3-hexadecylsulfoxy-2-hydroxypropyl) terephthalate
bis-(3-dodecylsulfoxy-2-hydroxypropyl) isophthalate
bis-(3-hexadecylsulfoxy-2-hydroxypropyl) isophthalate
bis-(3-dodecylsulfoxy-2-hydroxypropyl) phthalate
bis-(3-hexadecylsulfoxy-2-hydroxypropyl) phthalate
tris-(3-hexadecylsulfoxy-2-hydroxypropyl) trimellitate
tetrakis-(3-hexadecylsulfoxy-2-hydroxypropyl) pyromellitate In oversimplified form, these novel beta-hydroxysulfoxides are obtained by a selective intra-molecular oxidation reaction of β-hydroperoxy sulfides which result from the reaction of an alpha olefin and thiol using molecular oxygen and actinic radiation, which can be ultraviolet light or visible light, in the presence of a dye sensitizer. If visible light is used, the dye sensitizer can be selected from the group consisting of methylene blue, Eosin, and Rose Bengal. Ketones in general, such as acetone, can also act as sensitizers.

In general, the reaction with molecular oxygen is carried out with an olefin: thiol mixture wherein the ratio can be from 1:1 to 5:1 moles of thiol to moles of carboxyallyl functions, preferred ratio of 1:1. Reactions are run in a solvent such as benzene, cyclohexane or n-heptane at −20° to +40° C. under air at 1 to 20 atmospheres pressure, or oxygen pressure at 5.0 to 200 psig for 2 to 400 hours. Preferred conditions are 15° to 30° C. under oxygen at 20 to 50 psig for 8 to 100 hours. The reaction below 15° C. tends to be very slow. As the temperature is increased above the range from about 15° to 40° C., there is a tendency for the β-hydroxy peroxide sulfide to decompose under the conditions of the reaction. A dye such as methylene blue, or Rose Bengal in acetone solution is added to give concentrations of 0.001 to 1.0% by weight; preferred is 0.05 to 0.5% by weight. A convenient method of running the reaction is by shaking the reaction mixture in a pressure bottle in a Parr Pressure Reaction Apparatus under illumination from the source of actinic radiation (visible or ultraviolet light) such as a photoflood lamp, a sun lamp, or a 300–500 watt light bulb in a reflector. The reaction is continued until the absorption of oxygen slows or ceases. The filtered solutions are evaporated in a Rotovapor apparatus at 30° to 40° C. under 0.01 to 1 mm pressure.

In general, the allyl esters of arenepolycarboxylic acids, from which the sulfoxides are derived, can be prepared by any one of several procedures. Allyl alcohol can be reacted with the polycarboxylic acid in the presence of a protonic acid which can be sulfuric acid, p-toluene sulfonic acid, methane or ethane sulfonic acids, or mixtures thereof, or acidic resins which are sulfonated polystyrene resin. The polycarboxylic acid in the form of the sodium of silver salt can be reacted with allyl chloride or allyl bromide.

Any mercaptan can be employed although aliphatic and aromatic mono- or polymercaptans containing from about 1 to about 40 carbon atoms, and preferably from about 6 to 20 carbon atoms, are preferred. For bacteria growth control, better results are usually obtained with aliphatic mercaptans of from about 8 to 12 carbon atoms. Examples of suitable mercaptans are ethyl mercaptan, butyl mercaptan, hexyl mercaptan, octyl mercaptan, nonyl mercaptan, octadecyl mercaptan, thiophenol, thiocresols, 1-phenylhexane-6-thiol, cyclohexane thiol, p-menthane-thiol, pyridine-2,3-, and 4-thiols, and quinoline-4-thiol.

Although the herein described derivatives all exhibit to a definite degree anti-rust properties, surfactant properties, and bacterial growth control properties, all are not necessarily equivalent in their effectiveness, since, depending upon the nature and severity of the service in which they are used, some variation in effectiveness may be exhibited.

In summary, the invention consists of a family of poly sulfoxides which are prepared by the oxidation of thioethers prepared by reacting allyl esters of arene polycarboxylic acids with thiols in the presence of actinic radiation and a dye sensitizer. The thiol can be an alkyl thiol, an aralkyl thiol, an alkylated aryl thiol, an unsaturated heterocyclic thiol and a cycloalkyl thiol. The alkyl moiety of said thiols can be selected from the group consisting of methyl, ethyl, propyl, isopropyl, butyl, isobutyl, 2-ethylhexyl, amyl, hexyl, heptyl, dodecyl, octyl, isotridecyl, stearyl, oleyl, tetracosyl moieties. The said alkyl moiety can be terminated by a group selected from the group consisting of hydrogen, phenyl, biphenyl, naphthyl, anthranyl, thienyl, pyridyl, benzothienyl, thienobenzyl, quinolyl, isoquinolyl, dibenzothienyl, phenanthridyl, cyclohexyl, cycloheptyl, cyclooctyl, decahydronaphthalene, perhydroanthracene, perhydrophenanthrene radicals, said radicals when substituted, being substituted with substituents selected from the group consisting of halogens (fluorine, chlorine, bromine, iodine), nitro, and alkoxies such as methoxy, ethoxy, propoxy, butoxy, decyloxy and dodecyloxy moieties. Examples of suitable thiols are ethyl mercaptan, butyl mercaptan, hexyl mercaptan, octyl mercaptan, nonyl mercaptan, octadecyl mercaptan, thiophenol, thiocresols, 1-phenyl-hexane-6-thiol, cyclohexanethiol, p-menthane-thiol, pyridine-2,3 and 4-thiols, and quinoline-4-thiol.

The preparation of the above-described reaction products is illustrated by the following examples, which are given by way of illustration and are not intended to limit the scope of the invention.

EXAMPLE I

A mixture of 12.4 g (50 mm) of diallyl terephthalate, 20.2 g (100 mm) of n-dodecanethiol, 100 ml of benzene, and 10 ml of 0.5% Rose Bengal in acetone was shaken under 24 psig. $O_2$ in a Pressure Reaction Apparatus, Parr Instrument Co., Moline, Illinois, and irradiated with a 500 watt light bulb in a reflector about 15 cm from the shaker. The mixture absorbed 9 lbs. $O_2$ in 32 hours. It was filtered and evaporated in a rotary evaporator at 40° C. and 0.3 Torr to give 28.3 g of yellow product.

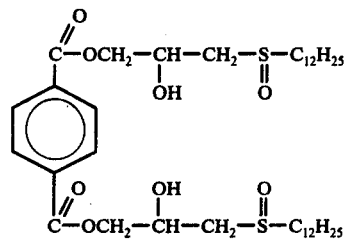

Analysis: $C_{38}H_{66}S_2O_8$:
Calculated: C, 63.9%, H, 9.2%, S, 9.0%.
Found: C, 64.1%, H, 9.4%, S, 9.1%.

EXAMPLE II

A mixture of 12.4 g (50 mm) of diallyl terephthalate, 25.85 g (100 mm) of n-hexadecylthiol, 100 ml of benzene, and 10 ml of 0.5% Rose Bengal in acetone was treated as in Example I. It absorbed 8.5 lb. $O_2$ in 32 hours. The mixture was filtered and evaporated in a rotary evaporator at 40° C. and 0.2 Torr. to give 39.5 g light yellow solid product.

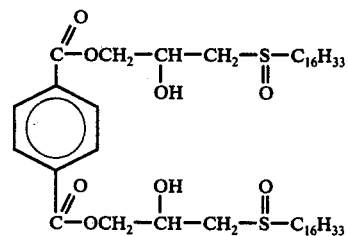

Analysis: $C_{46}H_{82}S_2O_8$:
Calculated: C, 66.8%, H, 9.9%, S, 7.7%.
Found: C, 66.9%; H, 9.9%, S, 7.4%.

EXAMPLE III

A mixture of 12.4 g (50 mm) of diallyl isophthalate, 20.2 g (100 mm) of n-dodecane-thiol, 100 ml of benzene, and 10 ml of 0.5% Rose Bengal in acetone was treated as described in Example I. It took up 8.5 lb. $O_2$ in 72 hours and gave 38.1 g of viscous, yellow product that analyzed C, 63.9%, H, 9.0%; S, 8.8%.

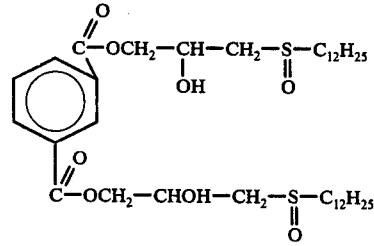

Analysis: $C_{38}H_{66}S_2O_8$:
Calculated: C, 63.9%; H, 9.2%; S, 9.0%.
Found: C, 63.9% H, 9.0%; S, 8.8%.

EXAMPLE IV

A mixture of 12.4 g (50 mm) of diallyl isophthalate, 25.85 g. (100 mm) of n-hexadecylthiol, 100 ml of benzene, and 10 ml of 0.5% Rose Bengal in acetone was treated as in Example I. It took up 8.6 lb. $O_2$ in 47 hours and gave 41.4 g of product that analyzed C, 67.2%, H, 9.8%, S, 7.4%.

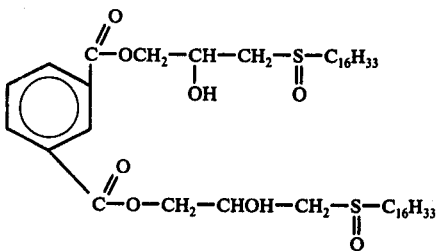

Analysis: $C_{46}H_{82}S_2O_8$:
Calculated: C, 66.8%, H, 9.9%; S, 7.7%.
Found: C, 67.2%; H, 9.8%; S, 7.4%.

EXAMPLE V

A mixture of 12.4 g (50 mm) of diallyl phthalate, 20.2 g (100 mm) of n-dodecanethiol, 100 ml of benzene, and 10 ml of 0.5% Rose Bengal in acetone was treated as in Example 1. It took up 8.5 lb. $O_2$ in 96 hours and gave 34.6 g of product that analyzed C, 64.2%; H, 9.0%; S, 9.1%.

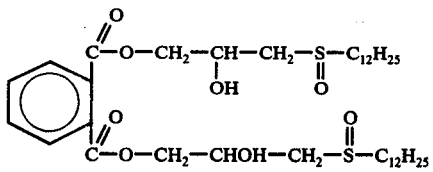

Analysis: $C_{38}H_{66}S_2O_8$:
Calculated: C, 63.9%, H, 9.2%; S, 9.0%.
Found: C, 64.2%; H, 9.0%, S, 9.1%.

EXAMPLE VI

A mixture of 12.4 g (50 mm) of diallyl phthalate, 25.85 g (100 mm of n-hexadecyl thiol, 100 ml of benzene and 10 ml of 0.5% Rose Bengal in acetone was treated as in Example I. It absorbed 8.6 lb. $O_2$ in 69 hours and gave 39.5 g of product that analyzed C, 67.3%, H, 10.1%; S, 7.5%.

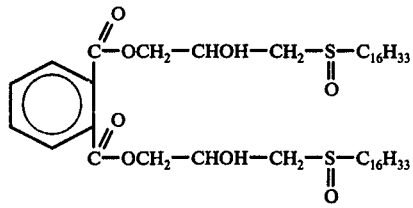

Analysis: $C_{46}H_{82}S_2O_8$:
Calculated: C, 66.8%; H, 9.9%; S, 7.7%.
Found: C, 67.3%; H, 10.1%, S, 7.5%.

EXAMPLE VII

A mixture of 8 g (25 mm) of triallyl trimellitate, 19.39 g (75 mm) of n-hexadecyl thiol, 75 ml n-heptane, and 10 ml of 0.5% methylene blue in acetone was treated as in Example I. It absorbed 4 lb. $O_2$ in 48 hours and gave 34.1 g of white, waxy product.

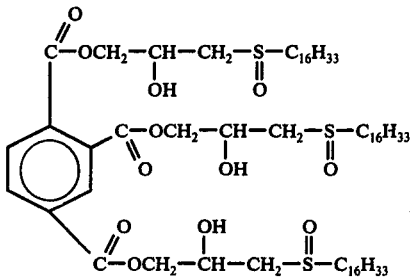

Analysis: $C_{66}H_{120}S_3O_{12}$:
Calculated: C, 66.0%; H, 10.0%; S, 8.0%.
Found: C, 65.9%; H, 10.4%; S, 8.1%.

EXAMPLE VIII

A mixture of 12.42 g (30 mm) of tetra-allyl pyromellitate, 43 g (120 mm) of n-hexadecylthiol, 75 ml of n-heptane, and 10 ml 0.5% methylene blue in acetone was treated as in Example I. It absorbed 7.5 lb. $O_2$ in 100 hours and gave 58.6 g of pale yellow, waxy solid.

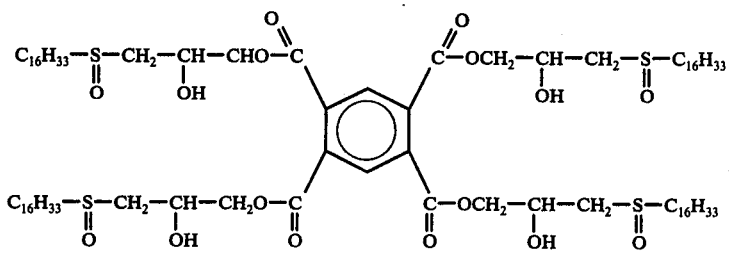

Analysis: $C_{86}H_{158}S_4O_{16}$:
Calculated: C, 65.6%; H, 10.0%; S, 8.1%.
Found: C, 65.8%, H, 10.3%; S, 7.7%.

EXAMPLE IX

The effectiveness of the novel compounds of my invention as surfactants in lowering interfacial tension between solvent-extracted 5W oil and water was measured, using a Cenco-Du Nouy Interfacial Tensiometer #70545 with a 6 cm platinum-iridium ring at 25° C., with double-distilled water, with these results.

| Product of Example No. | Concentration, % | Dynes/cm |
|---|---|---|
| Control (water only) | 0 | 34.03 |
| I | 1 | 8.16 |
| II | 1 | 0 |
|  | 0.5 | 0 |
|  | 0.25 | 4.5 |
| III | 1 | 7.8 |
| IV | 1 | 0.3 |
| V | 1 | 6.18 |
| VI | 1 | 1.34 |
| VII | 0.8 | 0 |
| VIII | 0.4 | 2.5 |
|  | 1 | 2.38 |

The data shows that my compounds are effective in lowering interfacial tension, particularly the compounds of Examples II, IV, and VII.

EXAMPLE X

The novel compounds of my invention were tested as rust inhibitors in 5W SX oil at 0.5 wt.% in the ASTM D-665 rust test, with these results. Ten is zero rust, 1 is heavy, complete rust.

| Compound, Example # | Rust Rating |
|---|---|
| I | 10 |
| II | 9.5 |
| III | 4 |
| IV | 10 |
| V | 4 |
| VI | 7 |

EXAMPLE XI

The compounds of Examples I through VIII were tested as biocides and inhibitors for the growth of micro-organisms by this test: 25 g of agar preparation were placed in standard Petri dishes. The agar preparation consisted of 23.5 g of Bacto Plate Count Agar, Difco Laboratories, Detroit, Michigan, dissolved in 1 liter of water. Plate count Agar contains a standard USP formula for nutrient agar, consisting of

| | |
|---|---|
| 5 g | Pancreatic digest of casein |
| 2.5 g | Yeast extract |
| 1 g | Glucose |
| 15 g | Agar |

Four Petri dishes were untreated and used as blanks. To the others, in duplicate, were added 2.5 ml of 1% acetone solutions of the products of Examples I–VIII. All plates were uncovered for 4 hours to expose them to the spores of adventitious fungi and bacteria, then covered and stored at 30° C. for 6 days. Ratings were given at this point; 0 represents no growth, 5 shows luxuriant colonies of fungi and bacteria. Results are shown in the table.

| Product, Example # | Rating |
|---|---|
| Control | 5,5 |
| I | 0,0 |
| II | 0,0 |
| III | 0,0 |
| IV | 1,1 |
| V | 0,1 |
| VI | 1,1 |
| VII | 0,0 |
| VIII | 0,0 |

The β-hydroxysulfoxides from allyl arenepolycarboxylates of my invention can be used in pesticide solutions and formulations at 0.001% to 10% by weight.

EXAMPLE XII

The compounds of Examples I–VIII were tested as additives for tertiary oil recovery in a vial test. In this test 1 part of each of the compounds in Examples I-- VIII was mixed with 10 parts of polybutene sulfonate. The mixture, 5 g, was stirred into 45 g of 0.2 N saline solution (NaCl) representing naturally-occurring brine in oil-well formation. Crude oil, 5 g, was added and the mixtures shaken, then stored at 25° C. All the novel compounds of my invention gave stable emulsions.

EXAMPLE XIII

Four-ball wear tests were run on solutions of the products of Examples IV and VIII at 1.0% by weight in solvent-extracted 5W oil. The ASTM D-2266 test for anti-wear additives was followed with these slight modifications: 600 rpm, 200° F, 2 hours at 40 kg load. Under these conditions SX-5 oil gives a wear scar of about 0.7 mm. The results were:

| Product | Wear Scar, mm |
|---|---|
| Example IV | 0.66 |
| Example VIII | 0.46 |

A good zinc dithiophosphate at 1 wt.% gives a wear scar of about 0.45 mm or less. The product of Example VIII is particularly noteworthy as it contains no metal.

What is claimed is:

1. Poly (2-hydroxy-3-alkylsulfoxypropyl-1)$_n$ esters of arene polycarboxylic acids wherein the said esters are of the formula

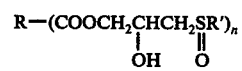

wherein $n$ is 2 to 6, R is an n-valent radical derived from benzene, biphenyl, naphthalene, anthracene or phenanthrene wherein R can be substituted by nitro, halogen and alkoxy of 1 to 12 carbon atoms and R' is selected from the group consisting of alkyl moieties containing from 1 to 22 carbon atoms, and aralkyl moieties, alkylated aryl moieties and cycloalkyl moieties containing 4 to 40 carbon atoms, the ring radicals of said moieties being selected from the group consisting of phenyl, biphenyl and cyclohexyl radicals, where R' can be substituted with nitro, halogen and alkoxy of 1 to 12 carbon atoms.

2. The compound of claim 1 which is bis-(3-dodecylsulfoxy-[3]2-hydroxypropyl) terephthalate.

3. The compound of claim 1 which is bis-(3-hexadecylsulfoxy-2-hydroxypropyl) terephthalate.

4. The compound of claim 1 which is bis-(3-dodecylsulfoxy-2-hydroxypropyl) isophthalate.

5. The compound of claim 1 which is bis-(3-hexadecylsulfoxy-2-hydroxypropyl) isophthalate.

6. The compound of claim 1 which is bis-(3-dodecylsulfoxy-2-hydroxypropyl) phthalate.

7. The compound of claim 1 which is bis-(3-hexadecylsulfoxy-2-hydroxypropyl) phthalate.

8. The compound of claim 1 which is tris-(3-hexadecylsulfoxy-2-hydroxypropyl) trimellitate.

9. The compound of claim 1 which is tetrakis-[3] (3-hexadecylsulfoxy-2-hydroxypropyl) pyromellitate.

* * * * *

UNITED STATES PATENT OFFICE
CERTIFICATE OF CORRECTION

Patent No. 4,095,029  Dated June 13, 1978

Inventor(s) Ellis K. Fields

It is certified that error appears in the above-identified patent and that said Letters Patent are hereby corrected as shown below:

Column 10, line 47, "sulfoxy - [3]2" should be -- sulfoxy - 2 --

Column 10, line 61, "tetrakis[3]" should be -- tetrakis- --

Signed and Sealed this

Eighth Day of May 1979

[SEAL]

Attest:

RUTH C. MASON
*Attesting Officer*

DONALD W. BANNER
*Commissioner of Patents and Trademarks*